(12) United States Patent
Lappe et al.

(10) Patent No.: US 6,964,752 B2
(45) Date of Patent: *Nov. 15, 2005

(54) SYSTEM FOR AUTOMATICALLY TESTING A FLUID SPECIMEN

(75) Inventors: Murray I. Lappe, Beverly Hills, CA (US); David A. Birkner, Wayland, MA (US); John W. Goodin, Coto de Caza, CA (US); Keith Patten, Los Angeles, CA (US); Bill Whitford, Woodland Hills, CA (US)

(73) Assignee: eScreen, Inc., Overland Park, KS (US)

( * ) Notice: Subject to any disclaimer, the term of this patent is extended or adjusted under 35 U.S.C. 154(b) by 120 days.

This patent is subject to a terminal disclaimer.

(21) Appl. No.: 10/779,014

(22) Filed: Feb. 13, 2004

(65) Prior Publication Data

US 2004/0166023 A1 Aug. 26, 2004

Related U.S. Application Data

(60) Division of application No. 10/072,154, filed on Feb. 6, 2002, now Pat. No. 6,716,393, which is a division of application No. 09/444,926, filed on Nov. 24, 1999, now Pat. No. 6,514,461, which is a continuation-in-part of application No. 09/245,175, filed on Feb. 5, 1999, now Pat. No. 6,342,183, which is a continuation-in-part of application No. 09/025,559, filed on Feb. 18, 1998, now Pat. No. 5,902,982, and a continuation-in-part of application No. 09/018,487, filed on Feb. 4, 1998, now Pat. No. 6,036,092, and a continuation-in-part of application No. 08/832,957, filed on Apr. 4, 1997, now Pat. No. 5,929,422, and a continuation-in-part of application No. 08/801,041, filed on Feb. 14, 1997, now Pat. No. 5,916,815.

(51) Int. Cl.$^7$ ............................................. G01N 31/00
(52) U.S. Cl. ..................... 422/82; 422/68.1; 422/63; 422/82.05; 422/119; 422/58; 422/61; 422/100; 422/102; 422/103
(58) Field of Search ...................... 422/68.1, 63, 82.05, 422/119, 58, 61, 100, 102, 103

(56) References Cited

U.S. PATENT DOCUMENTS

| | | |
|---|---|---|
| 3,832,134 A | 8/1974 | Sohn |
| 3,849,256 A | 11/1974 | Linder |

(Continued)

Primary Examiner—Jill Warden
Assistant Examiner—Sam P. Siefke
(74) Attorney, Agent, or Firm—Hovey Wiliiam LLP

(57) ABSTRACT

A system for automatically testing a fluid specimen, e.g., urine, to indicate the presence of specified chemical components in the specimen. The system preferably utilizes an assaying device comprised of a collection cup and a cap which carries at least one test strip. The device includes an integrated aliquot delivery mechanism actuatable to wet the test strip with an aliquot delivered from the fluid specimen. The assaying device is configured to operate in conjunction with an electronic reader device capable of actuating the aliquot delivery mechanism and reading the reaction of the test strip. A preferred reader device defines a keyed receptacle for accommodating a complementary shaped cup housing in a particular orientation. The reader device is comprised of a camera for capturing the image of a test strip, an actuator for actuating an aliquot delivery mechanism, and a microprocessor/controller for (1) controlling the camera and actuator and (2) processing the image.

6 Claims, 8 Drawing Sheets

U.S. PATENT DOCUMENTS

| | | |
|---|---|---|
| 3,980,436 A | 9/1976 | Greenfield et al. |
| 4,040,791 A | 8/1977 | Kuntz |
| 4,042,329 A | 8/1977 | Hochstrasser |
| 4,059,407 A | 11/1977 | Hochstrasser |
| 4,070,249 A | 1/1978 | Janin et al. |
| 4,385,115 A | 5/1983 | de Zabala et al. |
| 4,435,504 A | 3/1984 | Zuk et al. |
| 4,454,235 A | 6/1984 | Johnson |
| 4,458,020 A | 7/1984 | Bohn et al. |
| 4,473,530 A | 9/1984 | Villa-Real |
| 4,557,274 A | 12/1985 | Cawood |
| 4,573,983 A | 3/1986 | Annis |
| 4,624,929 A | 11/1986 | Ullman |
| 4,690,801 A | 9/1987 | Anderson |
| 4,789,638 A | 12/1988 | Kramer et al. |
| 4,842,826 A | 6/1989 | Guala |
| 4,844,866 A | 7/1989 | Wallace et al. |
| 4,865,813 A | 9/1989 | Leon |
| 4,873,193 A | 10/1989 | Jensen et al. |
| 4,885,253 A | 12/1989 | Kralovic |
| 4,920,046 A | 4/1990 | McFarland et al. |
| 4,927,605 A | 5/1990 | Dorn et al. |
| 4,953,561 A | 9/1990 | Guirguis |
| 4,960,130 A | 10/1990 | Guirguis |
| 4,961,432 A | 10/1990 | Guirguis |
| 4,976,923 A | 12/1990 | Lipsky et al. |
| 4,978,502 A | 12/1990 | Dole et al. |
| 4,992,296 A | 2/1991 | Gibson |
| 5,003,988 A | 4/1991 | Guirguis |
| 5,009,235 A | 4/1991 | Messenheimer |
| 5,016,644 A | 5/1991 | Guirguis |
| 5,022,411 A | 6/1991 | Guirguis |
| 5,024,237 A | 6/1991 | Guirguis |
| 5,039,616 A | 8/1991 | Copelan |
| 5,119,830 A | 6/1992 | Davis |
| 5,133,935 A | 7/1992 | Copelan |
| 5,149,505 A | 9/1992 | English et al. |
| 5,186,897 A | 2/1993 | Eason et al. |
| 5,200,321 A | 4/1993 | Kidwell |
| 5,215,102 A | 6/1993 | Guirguis |
| 5,283,038 A | 2/1994 | Seymour |
| 5,316,732 A | 5/1994 | Golukhov |
| 5,320,808 A | 6/1994 | Holen et al. |
| 5,356,782 A | 10/1994 | Moorman et al. |
| 5,403,551 A | 4/1995 | Galloway |
| 5,408,535 A | 4/1995 | Howard, III et al. |
| 5,429,803 A | 7/1995 | Guirguis |
| 5,429,804 A | 7/1995 | Sayles |
| 5,464,775 A | 11/1995 | Smith |
| 5,490,971 A | 2/1996 | Gifford et al. |
| 5,496,736 A | 3/1996 | Stone |
| 5,501,837 A | 3/1996 | Sayles |
| 5,508,200 A | 4/1996 | Tiffany et al. |
| 5,516,638 A | 5/1996 | Urnovitz et al. |
| 5,541,059 A | 7/1996 | Chu |
| 5,591,401 A | 1/1997 | Sayles |
| 5,603,903 A | 2/1997 | Copelan |
| 5,640,969 A | 6/1997 | Davis |
| 5,770,458 A | 6/1998 | Klimov et al. |
| 5,849,505 A | 12/1998 | Guirguis |
| 5,850,468 A | 12/1998 | Yokoyama et al. |
| 5,902,982 A | 5/1999 | Lappe |
| 5,929,422 A | 7/1999 | Lappe |
| 5,942,407 A | 8/1999 | Liotta et al. |
| 5,976,895 A | 11/1999 | Cipkowski |
| 5,989,924 A | 11/1999 | Root |
| 6,074,606 A | 6/2000 | Sayles |
| 6,097,831 A | 8/2000 | Wieck et al. |
| 6,184,040 B1 | 2/2001 | Polizzotto et al. |
| 6,716,393 B2 * | 4/2004 | Lappe et al. ............... 422/68.1 |

* cited by examiner

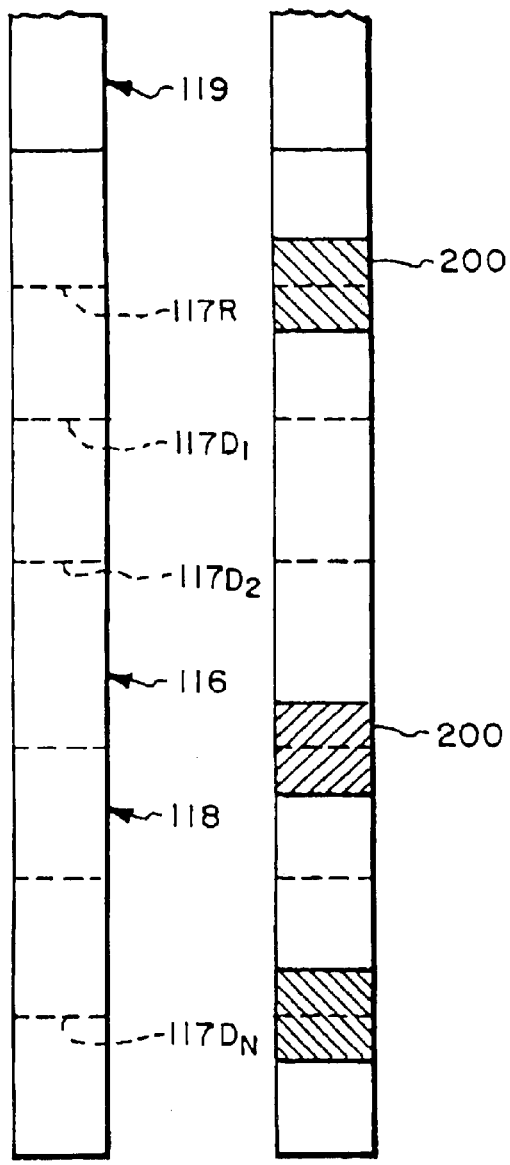
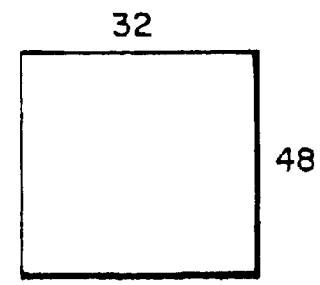
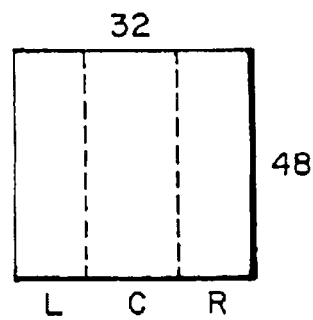
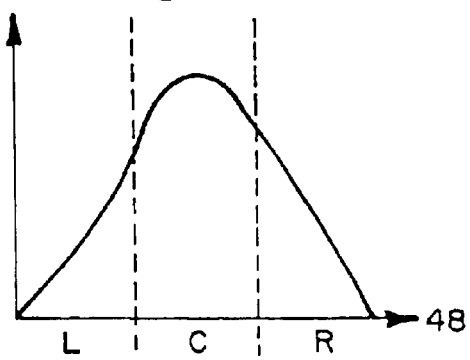
Fig.10A Fig.10B Fig.10C. Fig.10D. Fig.10E. Fig.10F.

SYSTEM FOR AUTOMATICALLY TESTING A FLUID SPECIMEN

RELATED APPLICATIONS

This application is division of U.S. application Ser. No. 10/072,154, filed Feb. 6, 2002, now U.S. Pat. No. 6,716,393 which is a division of U.S. application Ser. No. 09/444,926, now U.S. Pat. No. 6,514,461, filed Nov. 24, 1999, which is a continuation-in-part of U.S. application Ser. No. 09/245, 175, now U.S. Pat. No. 6,342,183 filed Feb. 5, 1999 by Murray Lappe, et al. is a continuation-in-part of U.S. applications Ser. No. 08/832,957 filed Apr. 4, 1997 now U.S. Pat. No. 5,929,422; Ser. No. 08/801,041 (now U.S. Pat. No. 5,916,8 15) filed Feb. 14, 1997; Ser. No. 09/018,487 filed Feb. 4, 1998, now U.S. Pat. No. 6,036,092 and Ser. No. 09/025,559 (now U.S. Pat. No. 5,902,982) filed Feb. 18, 1998. The disclosures of the aforementioned applications are, by reference, incorporated herein.

BACKGROUND OF THE INVENTION

This invention relates generally to systems for automatically testing fluid specimens, e.g. urine or other body fluids, to detect chemical substances or components therein. Such systems can be used, for example, to screen employee applicants for illegal drug use.

Employee drug testing typically involves an initial screening test to identify specimens which are negative (i.e., no drugs present). This test is usually performed with a low cost immunoassay which is very sensitive to small quantities of drug metabolites. If a drug metabolite is detected (referred to as "presumptive positive"), the specimen is then subjected to a confirmation test which typically utilizes a highly specific test method, such as a gas chromatography/mass spectrometry (GC/MS), to identify the specific drug components in the specimen.

Traditionally, both the screening and confirmation tests were performed in a common facility, i.e., centralized laboratory. More recently, systems have been implemented which perform the screening test at a local service site. They typically employ drug test kits which follow the tradition of home pregnancy test kits, i.e., they detect the presence of a specific drug substance(s) in a urine specimen. Such drug test kits generally identify, in human readable form, the drug(s) being tested to indicate the presence (or absence) of that drug. The screening test result with respect to each particular drug, and to the specimen as a whole, can either be (1) negative or (2) presumptively positive. If presumptively positive, then the specimen is generally sent to a remote laboratory for confirmation testing.

Inasmuch as disclosure of a presumptive positive test result can adversely impact an applicant's record and could potentially lead to litigation and employer liability, it is extremely important to prevent the inadvertent dissemination of test result data.

The aforementioned parent U.S. Pat. No. 6,342,183 describes an apparatus for locally analyzing a specimen to qualitatively detect specified chemical components therein. The apparatus includes an assaying device comprised of a cup for collecting a fluid specimen and a cap carrying at least one test strip for visually reacting to one or more specified chemical components in the specimen. The assaying device is preferably configured to interact with a reader device capable of reading the reaction of the test strip to produce an electronic data output.

More particularly, the apparatus described in application Ser. No. 09/245,175 includes an open cup defining an interior volume for accommodating a fluid specimen and an attachable cap configured for mounting on the cup to seal the interior volume. The cap carries at least one test strip and an integrated aliquot delivery mechanism actuatable to wet the test strip with an aliquot derived from the fluid specimen. The aliquot delivery mechanism preferably comprises a pump in the form of a plunger for forcing an aliquot of the fluid specimen onto the test strip. The plunger can be actuated either manually or automatically, e.g., by a piston controlled by a compatible reader device. The reader device preferably includes a microprocessor based controller for actuating the aliquot delivery mechanism, a camera for producing an image of the test strip, and a processor for analyzing the image to produce test result data. The test result data, along with identification data read from a label carried by the cap, can then be stored or communicated, e.g., via a modem.

SUMMARY OF THE INVENTION

The present invention is directed to an improved system and components thereof for automatically testing a fluid specimen, e.g. urine, saliva, or other body fluids, to indicate for the presence of specified chemical components in the specimen.

A system in accordance with the invention preferably utilizes an assaying device comprised of a collection cup and a cap which carries at least one test strip. The device includes an integrated aliquot delivery mechanism actuatable to wet the test strip with an aliquot derived from the fluid specimen. The assaying device is configured to operate in conjunction with an electronic reader device capable of actuating the aliquot delivery mechanism and reading the reaction of the test strip.

A preferred reader device in accordance with the invention preferably defines a keyed receptacle for accommodating a complementary shaped cup housing in a particular orientation. The reader device is comprised of a camera for capturing the image of a test strip, an actuator for actuating an aliquot delivery mechanism, and a microprocessor/controller for (1) controlling the camera and actuator and (2) processing the image.

In a preferred embodiment of the invention, the reader device preferably also includes a network connectivity device, e.g. modem, for enabling communication with a remote host computer. Although each reader device can operate independently as a stand-alone device, a preferred system in accordance with the inventor employs a host computer or server, which communicates, via a public and/or private network, with a plurality of reader devices located at separate service sites. Each service site can be configured to operate as a "thin client" with primary control being exercised by the host computer via the network. Alternatively, primary control can be exercised by the reader device at each site with only high level supervisory control coming from the host computer.

A preferred assaying device in accordance with the invention includes a cap carrying multiple test strips including at least one component test strip and at least one adulteration test strip. The cap is either formed of transparent material or is provided with transparent windows to permit external viewing of the test strips by the reader device camera. The cap preferably also carries one or more fiducial marks to facilitate image processing. Further, the cap preferably also carries machine readable identification information, e.g., a bar code label, to positively associate the specimen and test results with the correct individual. Preferably, the cap does not bear any human readable indicia identifying the specimen donor or indicating test results.

A preferred test strip for testing for the presence of specific chemical components is configured with multiple latent lines (i.e., markings) which can become visible when the strip is wetted. The lines preferably include a control or reference line and multiple drug lines each related to a different chemical component. If all of the latent lines visually appear within a certain test interval, e.g., up to eight minutes, after the strip has been wetted, this will indicate the absence of the specific chemical components sought. However, if any of those specific chemical components are present in concentrations above a certain threshold, their presence will suppress the appearance of one or more of the drug lines to indicate the presence of such chemical components.

A preferred reader device in accordance with the invention includes a camera located so that the cap is imaged onto the camera focal plane. The reader device includes a piston motor for driving a piston against the assaying device to deliver an aliquot to the test strips. The piston motor also moves a light shield into place around the cap enabling a light source to illuminate the cap to enhance the image for the camera.

A preferred automatic testing system in accordance with the invention operates as follows:

1. Fluid deposited into cup at local site; secure cap in tamper evident fashion;
2. Site administrator places assaying device, i.e., cup and cap, into "keyed" receptacle of local reader and enters ID information;
3. Reader alerts host computer via communication network;
4. Initiate automatic reader operational sequence:
   a. capture cap image and verify acceptability to proceed
   b. run piston motor to advance piston into assaying device to force fluid up channels to wet component and adulteration test strips
   c. capture cap image and verify acceptability to proceed
   d. periodically capture additional cap images during development interval up to about eight minutes
   e. analyze captured image data to determine
      1. test validity
      2. test results
   f. locally display test validity/results and/or communicate test validity/results to Host computer
   g. run piston motor to withdraw piston from cup
5. Site administrator removes cup from reader The camera produces a digital representation of the image incident on the camera focal plane. The processor then analyzes the digital representation to determine the color of the adulteration test strip and to locate visible markings on the component test strip coincident with the reference and drug lines. Image analysis is preferably performed by initially using fiducial marks on the cap to first precisely locate the cap image relative to a reference image. This can, for example, involve rotating, translating, and/or scaling the cap image. Thereafter, the digital representation of each test strip is examined to determine the presence (or absence) of drug lines. This involves first locating the strip reference line by effectively "drawing" a rectangular region around the reference line. The region can be considered as a rectangular matrix of pixels having rows extending across the strip width, each row being comprised of multiple column positions. For each row, the image is examined to determine whether the pixel at each column position exceeds a threshold. The sum of pixels exceeding the threshold is determined for each row. These row sums produce a graph whose x axis is related to the height (i.e., number of rows) of the region and whose y axis is related to the values of the individual row sums. A bell shaped curve will result whose peak locates the reference line. If no reference line is located, the test is terminated. If the reference line is located, then the examination continues in order to locate the drug lines. The detection of drug lines is more difficult because the amplitude, i.e., dark or light, of its pixels can vary widely dependent on several factors including wetting uniformity, urine color, variations amongst test strips, exposure time, etc. In order to compensate for these variations, each drug region is preferably divided into left, center, and right portions. A drug line is presumed to occupy the center portion of each region. However, its exact position and exact width can vary attributable to the aforementioned factors. Moreover, its brightness difference in relation to neighboring areas can be very subtle. Hence, a procedure is used to determine the weight of a line on a relative basis.

For example, for each drug region graph, the total area under each of three regions (left, center, right) is calculated. The left and right region areas are then numerically summed, and this resulting total area sum is multiplied by an experimentally determined "weighting value," thus producing a weighted sum. If the area of the center region is less than or equal to the weighted sum, no line is present. By using urine samples with known drug concentrations, a weighting value of 0.75 has been experimentally determined to produce very acceptable results.

BRIEF DESCRIPTION OF THE FIGURES

FIG. 10A is a diagrammatic view of a typical test strip used in embodiments of the present invention;

FIG. 10B is a diagrammatic view of the test strip similar to FIG. 10A but modified to represent rectangular regions used to locate reference and drug lines;

FIGS. 10C and 10D depict steps employed in analyzing a cap image to locate a strip reference line;

FIG. 10E depicts a step employed in analyzing a cap image to locate the presence of a strip drug line; and FIG. 10F is a drug region graph including a drug line centered in the graph.

DETAILED DESCRIPTION

Figure 1:
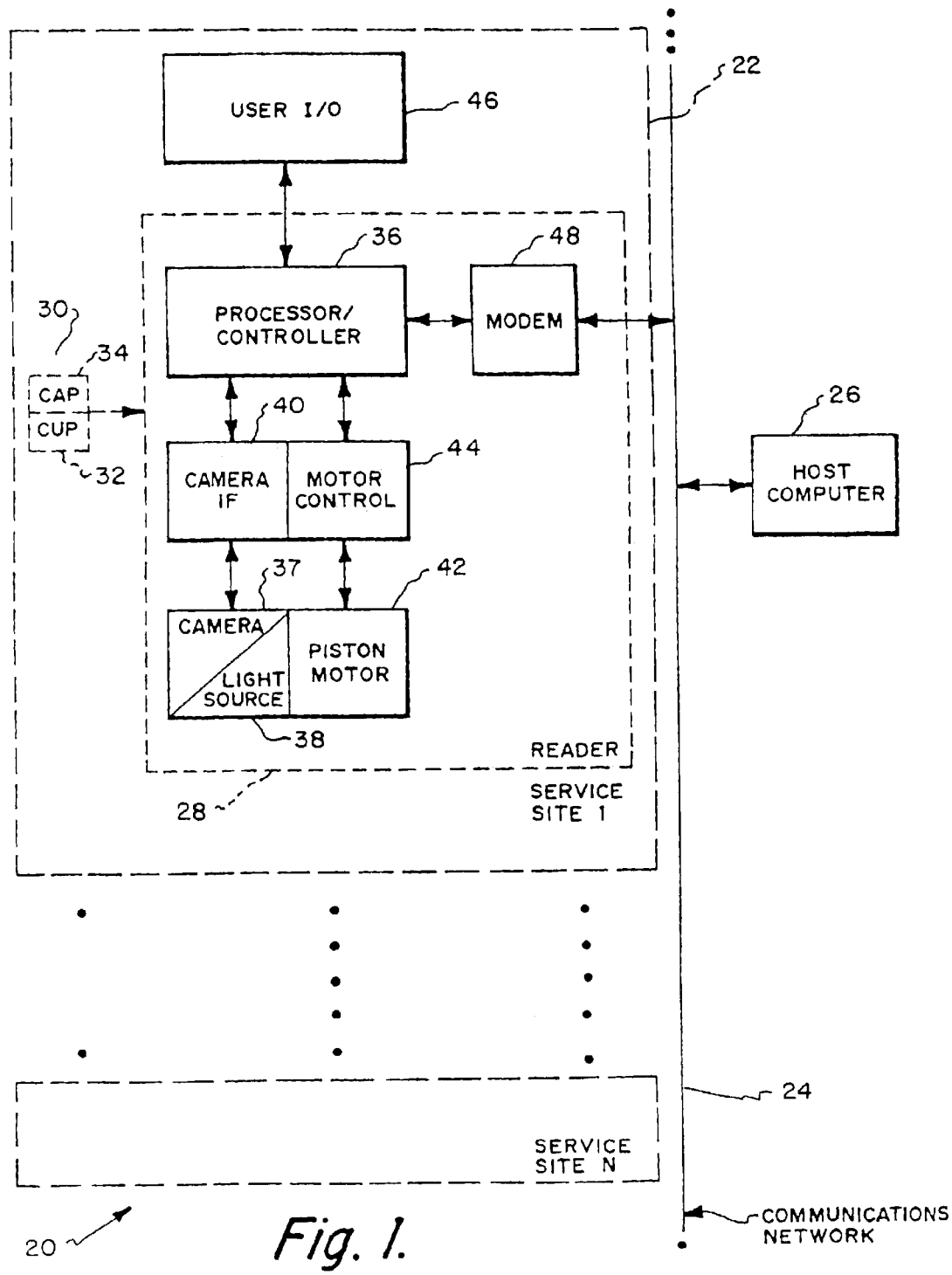
FIG. 1 is a block diagram of a system in accordance with the invention.

Attention is initially directed to FIG. 1 which depicts a preferred system 20 in accordance with the invention comprised of multiple service sites 22 respectively identified as 1 through N. Each service site can operate independently as a stand-alone system to perform a screening test, as will be described hereinafter. However, in accordance with a preferred system configuration, the multiple service sites are connected to a network 24, e.g., the Internet, for communication with a host computer 26.

Each service site includes a reader device 28 configured to cooperate with an assaying device 30 comprised of a specimen collection cup 32 and a cap 34. FIG. 1 depicts a functional block diagram of the reader 28 whereas FIGS. 2 and 4–7 illustrate the reader's structural configuration. The structural configuration of the assaying device 30 is illustrated in FIGS. 2–9.

Briefly, the reader 28 is comprised of a processor/controller 36 programmed to operate (1) a camera 37 and light source 38 via a camera interface circuit 40 and (2) a piston motor 42 via a motor control circuit 44. As will be discussed hereinafter, the piston motor 42 operates to deliver an aliquot from a specimen in the cup 32 to one or more test strips in the cap 34. The test strips each produce a visible reaction in response to being wetted by the aliquot. The camera 37 and light source 38 operate together to capture an image of the test strip(s) enabling the processor/controller 36 to process the image to determine test validity and whether the specimen is free of chemical components being monitored. The reader 28 preferably operates in conjunction with an input/output device 46 which enables a site attendant to enter information, e.g., donor identification information, via a device such as a touch pad or keyboard, and to view information, e.g. via an LCD display, provided by the processor/controller 36.

The processor/controller 36 is also preferably connected to the network 24 via a suitable connectivity device 48, e.g., a modem. This enables the reader to upload data, e.g., test results, billing information, etc. to the host computer 26. It also allows the host computer to exercise supervisory control over the processor/controller 36.

Figure 2:
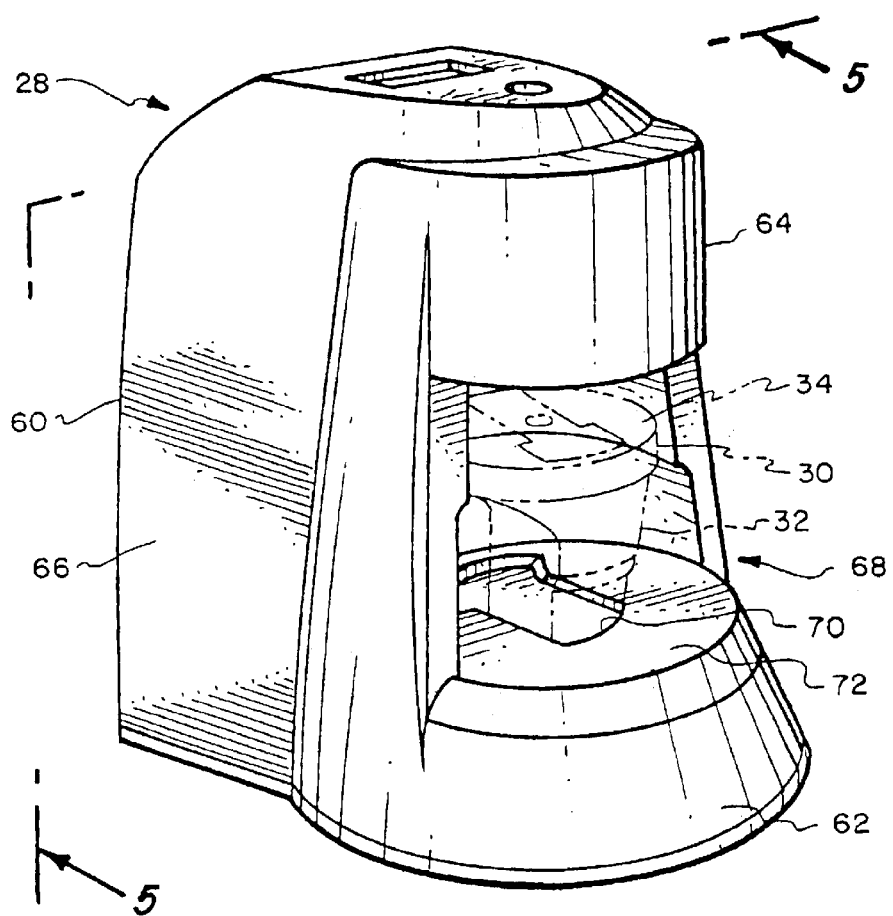
FIG. 2 is an isometric view of a preferred reader device in accordance with the present invention.

Attention is now directed to FIG. 2 which illustrates the exterior configuration of the reader housing 60. The housing is essentially comprised of a base portion 62, a head portion 64, and an enclosure portion 66, bridging the base and head portions. A receptacle 68 is defined between the base and head portions for receiving an assaying device 30 above a keyed recess 70 formed on base platform 72. The keyed recess 70 is shaped complementary to the lower periphery of the assaying device 30 to place the device in a specific orientation relative to head portion 64. The assaying device 30 is comprised of an open collection cup 32 and a detachable cap 34. The cup 32 defines an interior volume for collecting a fluid specimen, e.g. urine. After the fluid specimen has been deposited into the cup 32, the cap 34 is mounted thereon to seal the interior volume and prevent the fluid specimen from leaking. Inasmuch as each assaying device 30 is intended to be used only once to collect a single specimen, it is preferably fabricated via relatively low cost plastic molding processes.

Figure 3:
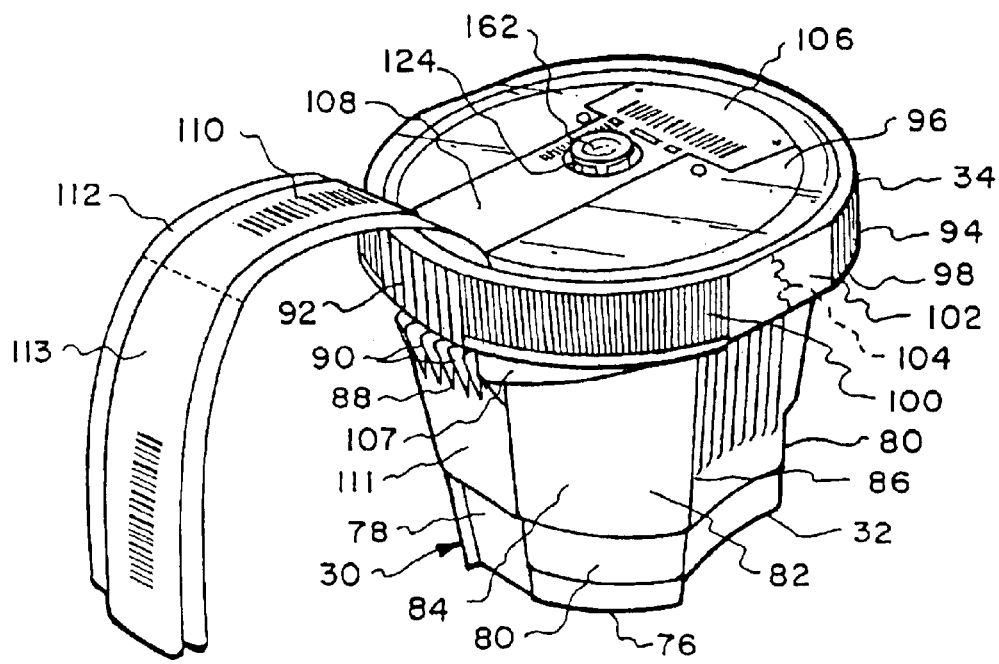
FIG. 3 is an isometric view of a preferred cup and cap.
Figure 4:
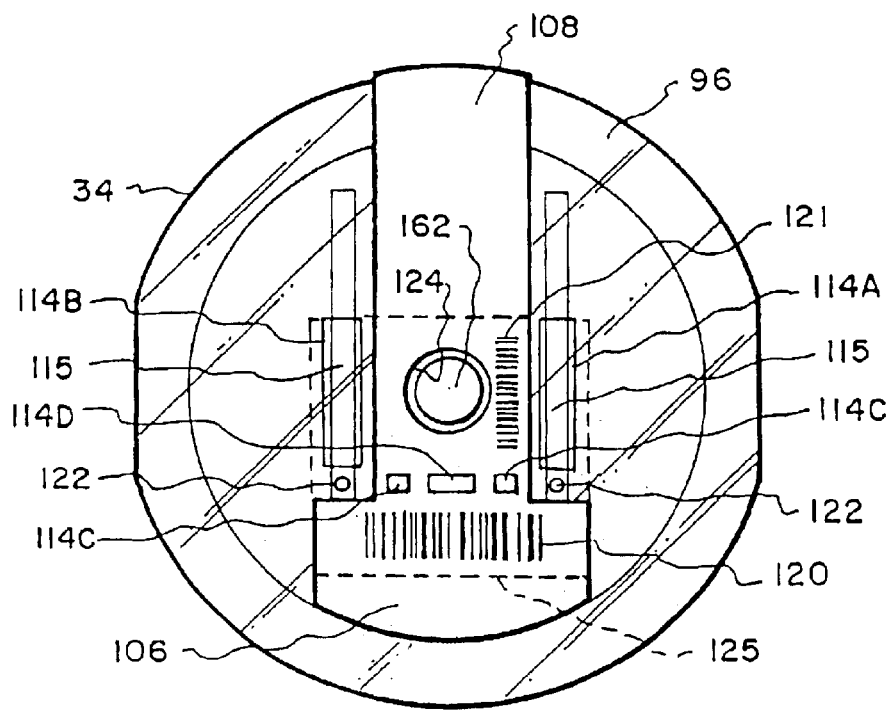
FIG. 4 is a plan view of the cap top surface.
Figure 5:
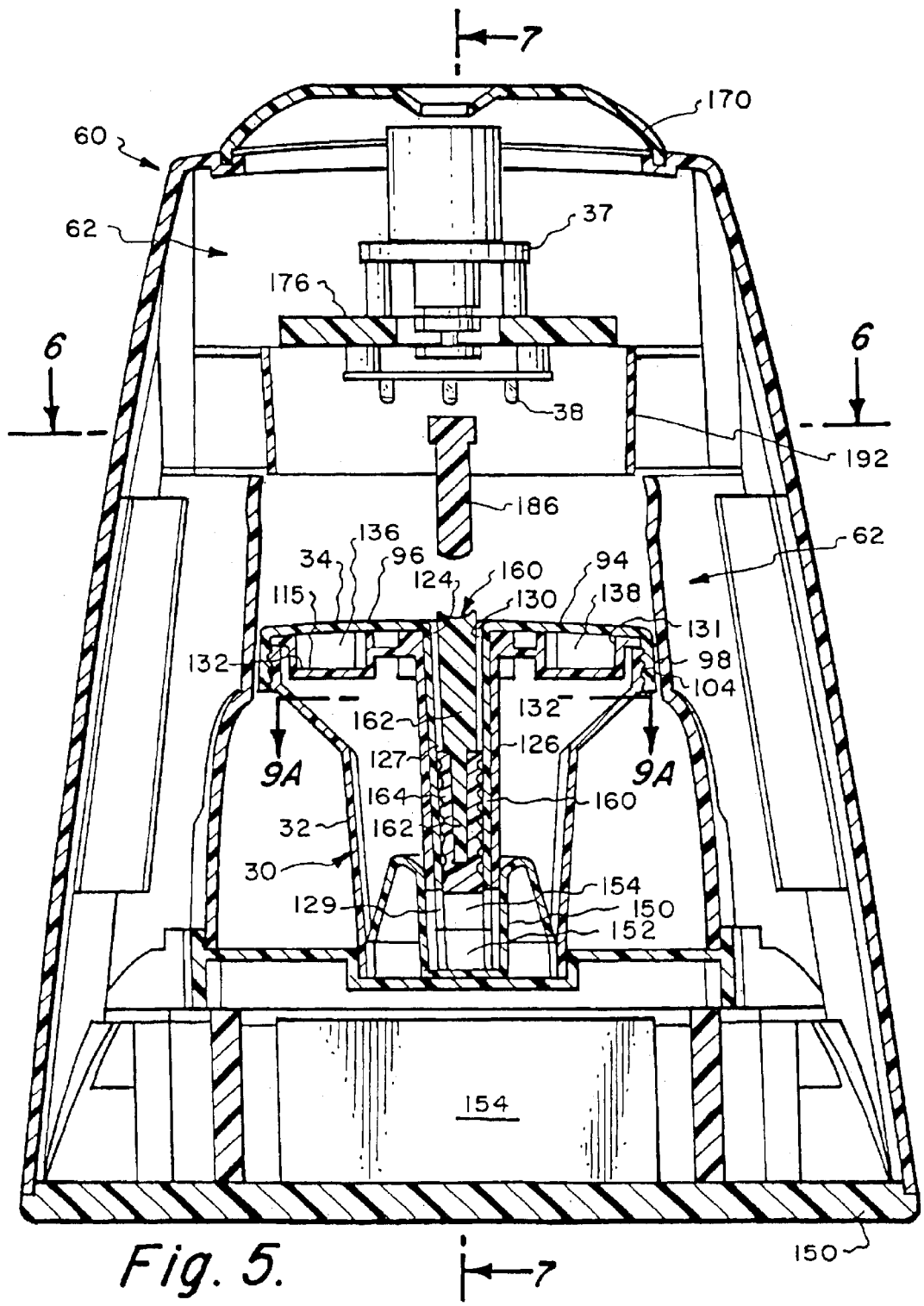
FIG. 5 is a front sectional view taken substantially along plane 5—5 of FIG. 2.
Figure 6:
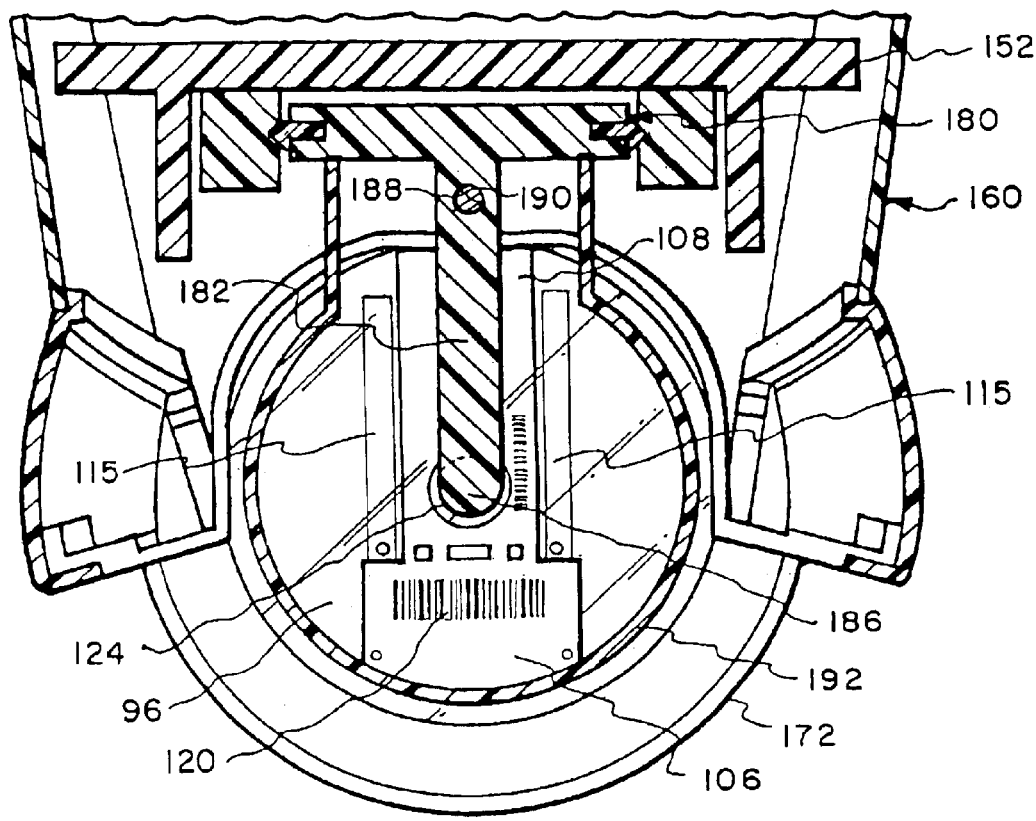
FIG. 6 is a top sectional view taken substantially along plane 6—6 of FIG. 5.
Figures 9A, 9B:
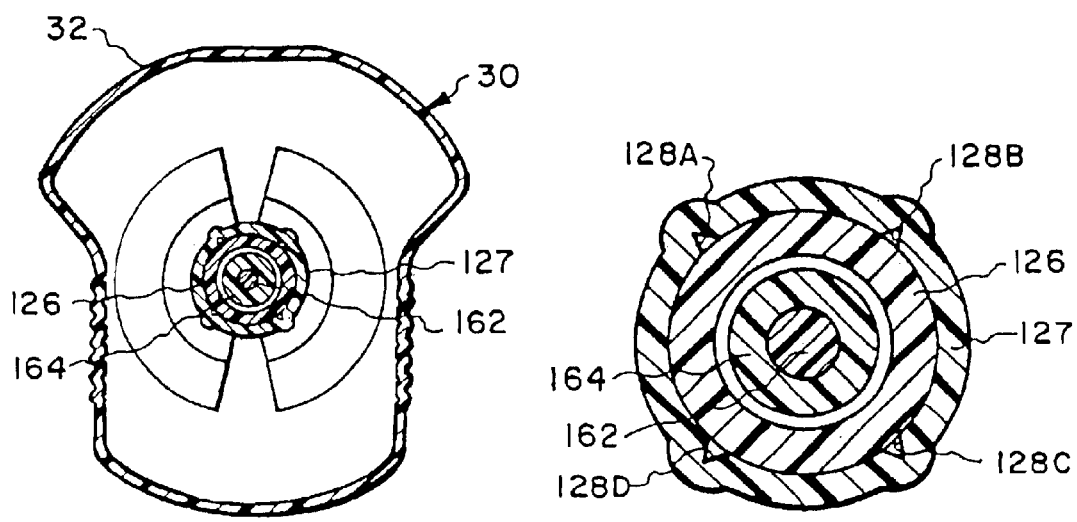
FIG. 9A is a sectional view taken substantially along the plane 9A—9A of FIG. 5 primarily showing the cup interior.
FIG. 9B is an enlarged sectional view showing the aliquot delivery mechanism of FIG. 9A in greater detail.

It can be noted in FIG. 3 that the cup 32 has an irregular lower periphery 76 particularly configured to mate with the keyed recess 70. The periphery 76 includes an enlarged front portion 78 and a reduced rear portion 80. The reduced rear portion 80 is bounded by flat finger grip sides 82 having raised surface features 84 extending to an oblique wall surface 86. This irregular configuration of the cup facilitates easy manual handling of the cup enabling it to be readily grasped by the hand of a user and/or administrator. The cup enlarged portion 78 preferably includes an area 88 characterized by multiple vertical fins 90. This area 88 functions as a key or registration area to which an index area 92 on the cap 34 is aligned to assure proper cap/cup sealing. Markings are preferably provided on the cup exterior to indicate maximum and minimum fill levels.

Briefly, the cap 34 is comprised of a substantially circular member 94 having a top exterior surface 96 and a depending flange or skirt 98. The skirt 98 has a primarily knurled outer surface 100 that preferably defines flat areas 102 and the aforementioned index area 92. The index area 92, which may be defined by vertical slots, is preferably used to align with the aforementioned cup area 88 to visually indicate to a user that the cap has been properly installed onto the cup. The cap 34 is preferably installed onto the cup via a mating thread 104. The cap 34 preferably carries a stop tooth 107 which rotates into engagement with the end fin 90 when the cap is properly installed onto the cup. When properly installed, the cap index area 92 will be aligned with the cup registration area 88. Alternative mounting mechanisms, e.g., bayonet mount, can be used to couple the cap 34 to the cup 32.

Provision is preferably made to include a tamper evident seal to immediately indicate to a user whether an assaying device, once sealed, has been tampered with. More particularly, note in FIG. 3 that the cap top surface 96 carries a label 106 having a first portion 108 permanently adhered to the surface 96. A second label portion 110 extends beyond the edge of cap 34 and is intended for sealing against cup area 111 immediately beneath the cup finned area 88. The label portion 110 carries a suitable adhesive on its undersurface which, prior to use, is protected by release paper 112. When the release paper is stripped away, label portion 110 can be sealed against cup area 111 to assure that cap 34 cannot be removed from cup 32 without that fact being immediately evident. The label 106 preferably also includes a perforated tear-off third portion 113 which can be affixed to a "B" container in case of split specimen collections, or in the event that a manual chain of custody record is required.

The cap top surface 96 (FIG. 4) is either transparent or at least defines one or more transparent areas 114, e.g., windows 114A, 114B, and 114C for enabling a test strip mounted beneath each window to be visible therethrough. As will be discussed hereinafter, the cap defines one or more compartments each of which accommodates a test strip 115 which, when wetted by a fluid specimen, reacts to provide a visual indication indicative of a characteristic of the specimen.

In the exemplary embodiment illustrated, the window 114C covers a test strip intended to detect specimen (1) authenticity and (2) adulteration. As is well known, a freshly voided urine specimen can be authenticated by a test strip which senses various characteristics including temperature and/or creatinine content of the specimen. Adulteration of the specimen can be detected by a test strip sensitive to exogenous components, e.g. pH and/or nitrites. Preferably, the test strip changes color when wetted and detection is achieved using a colormetric technique Larger windows 114A and 114B are intended to reveal test strips 115 for detecting various specific chemical components typically associated with illegal substance abuse. FIG. 10A schematically represents such a component test strip 116 showing multiple latent lines 117 visually represented on an indicator portion 118 extending from an absorbent portion 119. The latent lines 117 typically include one or more reference or control lines 117R and multiple drug lines $117D_1$, $117D_2$, etc., each for a different drug or chemical component to be detected. If all of the lines visually appear within a certain test interval, e.g., up to eight minutes, after the absorbent portion 119 has been wetted, this will indicate the absence of the specific chemical components sought (i.e., a "negative" test). However, if any one of those specific chemical components is present in concentration above a certain threshold, its presence will suppress the appearance of one or more of the lines to indicate to an astute observer and/or computer based reader, the presence of that component.

The cap top surface 96 (FIG. 4) preferably additionally defines a primary bar code area 120, a secondary bar code area 121, and one or more fiducial marks 122, to be discussed hereinafter. All of the windows 114, bar code areas, and fiducial marks are arranged around a plunger hole 124 within a tightly dimensioned image field 125 suitable for being imaged onto the focal plane of camera 37. In an exemplary embodiment, the image field has width and height dimensions respectively equal to 1446 mils and 1084 mils which is imaged onto a camera view field having 640 pixels horizontally and 480 pixels vertically.

The internal structure and operation of a suitable assaying device 30 is described in aforementioned parent U.S. Pat. No. 6,342,183, whose disclosure is, by reference, incorporated herein. Briefly, as depicted in FIGS. 5–9, the assaying device cap 34 defines descending concentric outer and inner tubular walls 126 and 127. Multiple passageways 128A, 128B, 128C, 128D extend vertically between the outer and inner tubular walls 126 and 127. Each passageway 128 defines a passageway inlet 129 at the lower end of inner tubular wall 127 and a passageway outlet 130 proximate to compartments 131, respectively accommodating component or adulteration test strips 132, located beneath the aforementioned windows 114. Overflow Basins 136, 138 are respectively located adjacent to the compartments beneath windows 114A, 114B to collect any fluid overflow.

The inner floor 150 of the cup 32 is configured to define an open well 152. When the cap 34 is installed on the cup 32, the lower end of the outer tubular wall 126 extends into the well 152 and essentially forms a closed chamber 154 for isolating a portion of the fluid specimen. A plunger 160, comprised of a plunger pin 162 and plunger element 164, is mounted in inner tubular wall 127 above chamber 154. The plunger element 164, is formed of soft conforming material able to seal against the inner surface of inner tubular wall 127. The opening 124 in the cap top surface 96 provides access to enable the pin 162 to be depressed.

As the plunger element 164 is depressed into chamber 154, the fluid therein is displaced upwardly via inlet 129 through multiple passageways 128. These passageways, 128A, 128B, 128C, 128D respectively extend to the aforementioned test strip compartments located below the aforementioned cap windows 114. Thus, depression of the plunger 160 within the inner tubular wall 127 displaces fluid from the chamber 154 to deliver an aliquot to each of the compartments 131, each compartment accommodating a separate strip 115 of test material. The device 30 is constructed and dimensioned so that each aliquot comprises a specific volume of fluid.

Attention is now directed to FIGS. 5–8 which illustrate the internal structure of the reader housing 60. The housing 60 is formed by a base plate 150 having a vertical frame member 152 secured thereto. The base plate 151 is weighted by block 154 for stability. A shell 160 is affixed to the base plate 150 and frame member 152. The shell includes a base platform member 72 which defines the aforementioned keyed recess 70. The shell 160 additionally includes a rear shell member 162 which encloses a rear compartment 164 housing the reader electronic circuit board(s) 166. An upper shell member 170 encloses a top compartment 172 which houses the camera 37, light source 38 and piston motor 42. These devices are structurally supported on arm 176 projecting forwardly from frame member 152.

Figure 7:
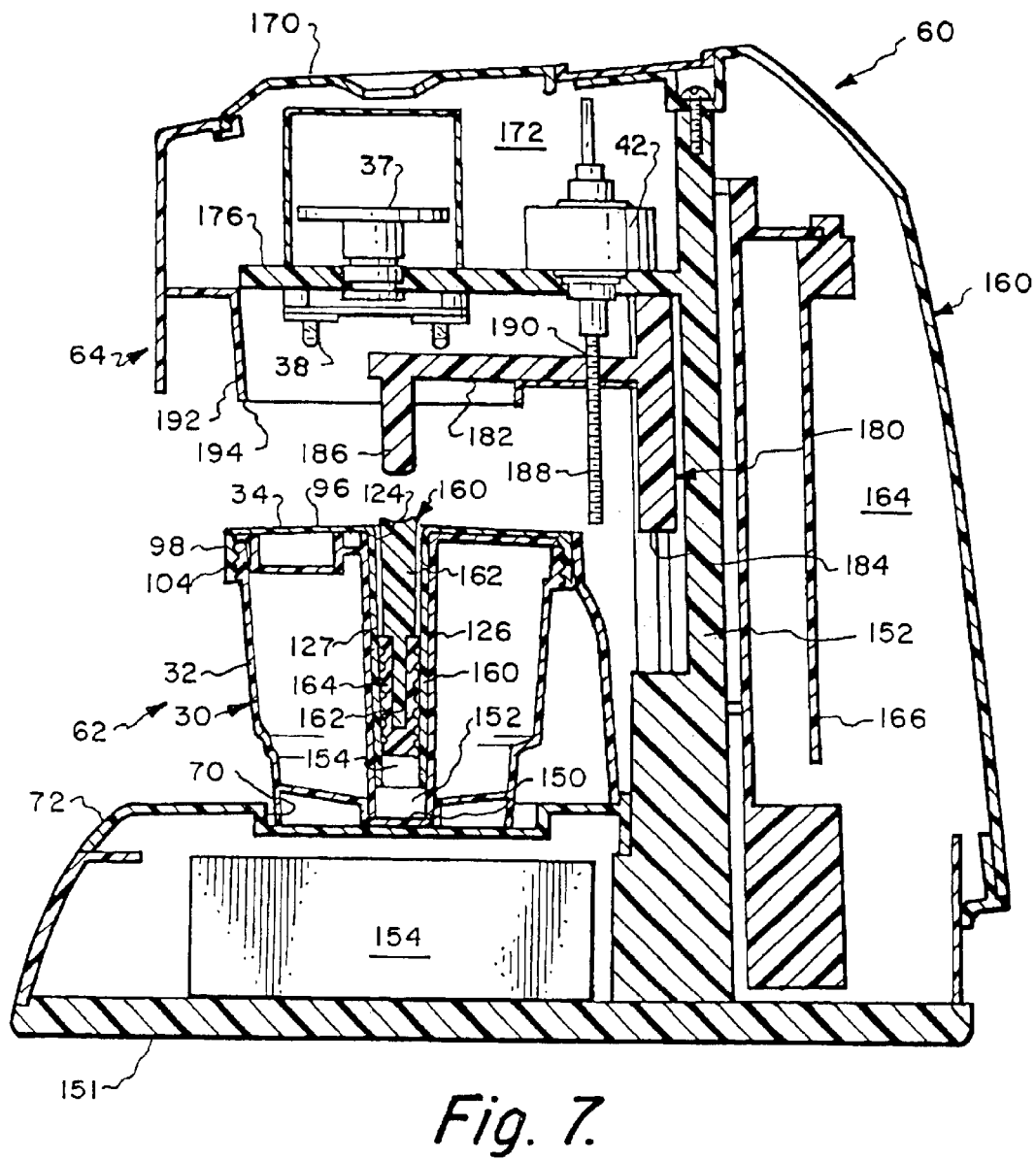
FIG. 7 is a side sectional view taken substantially along plane 7—7 of FIG. 5 showing the piston in its non-actuated position.
Figure 8:
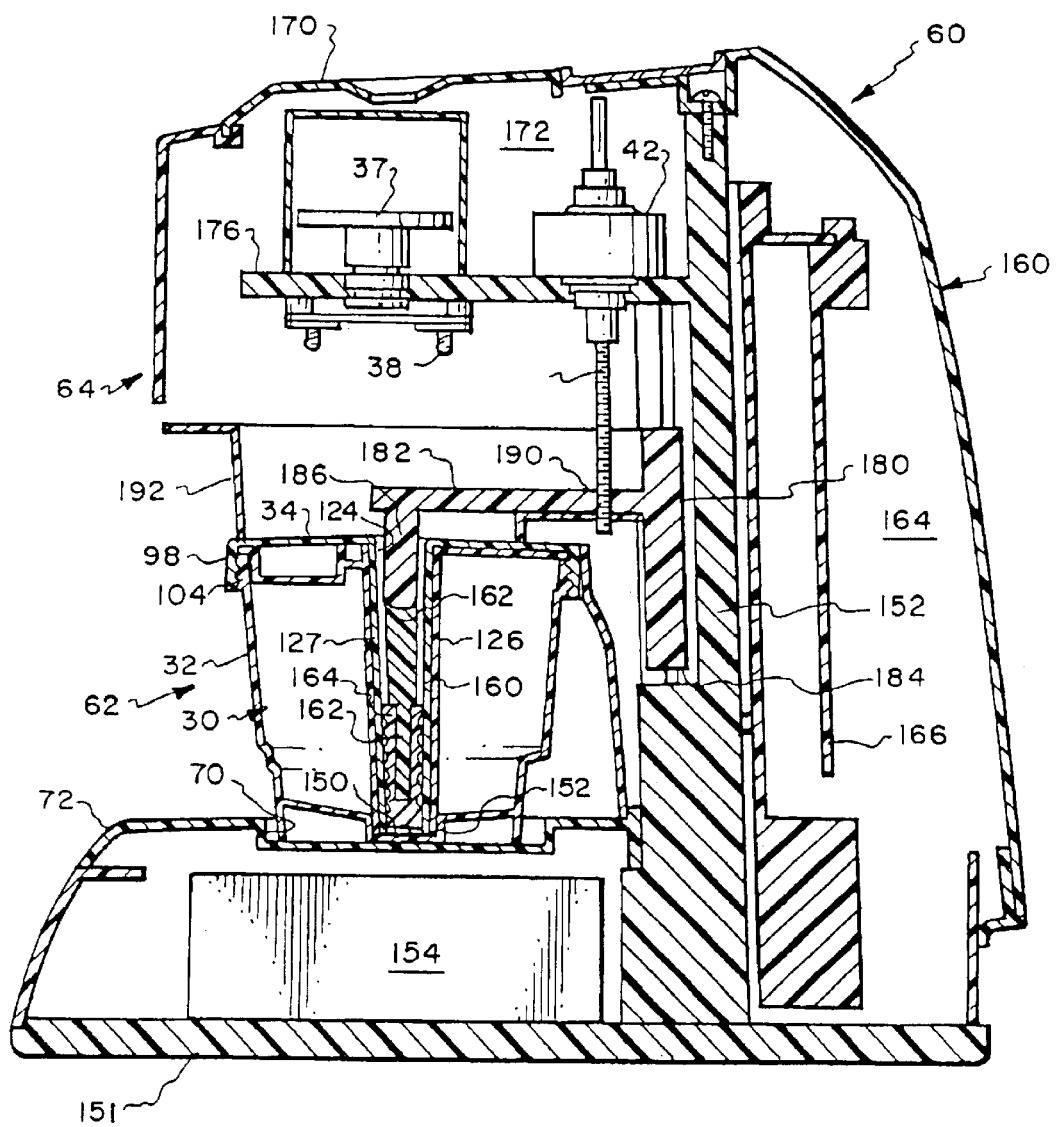
FIG. 8 is a side sectional view similar to FIG. 7 showing the piston in its actuated depressed position to force an aliquot to the cap for wetting the test strips.

A piston subassembly 180 is mounted for vertical reciprocal motion toward and away from base plate 150. The piston subassembly is comprised of a support arm 182 projecting forwardly from slide block 184 mounted for linear movement along guide rails 186. The support arm 182 carries a piston member 186 aligned with opening 124 in the cap of an assaying device 30 placed in the keyed recess 70. A lead screw 188 is threaded into hole 190 in support arm 182. The lead screw can be selectively rotated either clockwise or counterclockwise by piston motor 42 to move the slide block 184 either up or down. FIG. 7 depicts the piston member 186 in its up position providing sufficient clearance to allow an assaying device 30 to be placed on or removed from the keyed recess 70. FIG. 8 shows the piston member 186 in its down position extending into cap opening 124 to depress plunger 160 to displace fluid from the specimen in cup 32 to wet the test strips 115.

It should also be noted that the piston subassembly 180 includes a substantially cylindrical light shield 192 mounted on slide block 184. The light shield 192 defines a lower edge 194 which seals against the cap top surface 96 when the slide block is in its down position shown in FIG. 8.

The camera 37 can comprise a commercially available digital camera and appropriate optics for imaging the field 125 (FIG. 4) onto the camera's focal plane. The camera preferably has a resolution of 640 (horizontal) times 480 (vertical) pixels. Imaging is enhanced by selective illumination of light sources 38 and by the shielding effect afforded by light shield 192.

A preferred operational sequence for automatically testing a fluid specimen is represented by the following sequential steps:

1. Donor at a local site deposits fluid into cup 32; site administrator enters identification information and secures cap 34 in tamper evident fashion;
2. Administrator places cup/cap into "keyed" receptacle 70 of local reader 28 and enters ID information;
3. Reader 28 alerts host computer 26 via communication network 24;
4. Host computer 26 (or administrator) initiates reader operational sequence:
    a. camera 37 captures cap image and processor 36 verifies acceptability to proceed
    b. processor 36 runs piston motor 42 to advance piston 164 into cup to force fluid up channels 128 to wet component and adulteration test strips
    c. camera captures additional cap image and verify acceptability to proceed
    d. periodically capture additional cap images during development interval up to about eight minutes
    e. processor analyzes captured image data to determine
        1. test validity
        2. test results
    f. processor 36 displays test validity/results on local I/O 46 and/or communicates test validity/results to Host computer 26
    g. processor 36 runs piston motor to withdraw piston from cup
5. Site administrator removes cup from reader In step 1, the site administrator first enters donor and client (e.g., employer) information via I/O devices 46 into a database stored either in processor 36 or host computer 26. The donor voids into a cup 32 and the cap 34 is sealed thereon. The label is extended from the cap to the cup to assure that it is sealed in tamper evident fashion. Preferably the administrator and donor then initial the sealed label and review the chain of custody document. The donor and administrator both apply their signatures to the signature pad and a copy of the chain of custody document is printed and given to the donor. The donor is then dismissed. Preferably the cup/cap is then placed in the reader.

Step 4 of the foregoing sequence is automatically executed under the control of programmed microprocessor 36. In step 4a, the piston has not yet been inserted into the cup and may partially obscure the field of view. In addition, since the piston is not down, the light shield is only partially effective, and extraneous light may enter, further obscuring details. Nevertheless, an initial image is captured by the camera to examine the primary barcode 120 and other cap features to determine if it is valid. If the barcode is not valid, this fact is displayed to the site administrator for further action. An invalid barcode can indicate that the cup is inserted incorrectly, that there is no cup there at all, or that a "fake" cup has been inserted. If the administrator cannot resolve the issue and the barcode is indeed invalid, testing is aborted and the sealed cup is sent for laboratory analysis.

In step 4b, processor 36 runs the piston motor 42 to lower the piston 164 a predetermined distance. This also lowers the light shield 192 into place against the cap top surface 96 so that the light source 38 is then the only source of light illuminating the cap top. The light source 38 preferably comprises multiple green LED's inasmuch as the lines that appear on typical component test strips exhibit the highest contrast when viewed in green light. With the piston in its down position, it no longer obscures any cap features within the image field 125.

In step 4c, another image of the cap is captured and processed to double-check the primary barcode results from the previous step and to read the secondary barcode 121 and the fiducial marks 122. The fiducial marks 122 are small features printed on the cap directly above the test strip windows 114A, 114B and serve as reference points for subsequent processing steps to assure accurate image analysis. Preferably, the barcode labels have their own fiducial marks, which allow the barcodes to be found and read even if the label is askew. If all barcodes and fiducial marks can be located and properly read, then operation proceeds to step 4d. Otherwise, the site administrator is alerted and he/she decides whether to proceed or not.

The test strips take between two and eight minutes to develop. During step 4d, images are periodically captured and during step 4e, the images are processed and analyzed. Steps 4d and 4e are executed in an iterative loop. If all latent lines become visible after two minutes, the test is concluded and operation proceeds to step 4f. Otherwise steps 4d and 4e are executed every minute until eight minutes have elapsed. If any of the drug or control lines do not become visible, the assaying device is sent to the lab for further analysis.

The image analysis executed in step 4e includes an extensive procedure to be discussed hereinafter for discerning a color change on the adulteration test strip and visible reference and drug lines on the component test strip. The detection of these lines can be reasonably challenging because the amplitude, i.e., dark or light, of its pixels can vary widely dependent on several factors including variations in test strips, in wetting, in urine color, etc. In order to produce an optimum image for analysis, a sequence (e.g., 8) of images is actually captured. These multiple images are then mathematically summed divided by the number of images in order to produce an integrated image in which the random electrical and optical "noise" has been reduced by this "averaging" process. This integrated image is then used in the subsequent line detection procedure:

4e(1) The fiducial marks 122, which had been found to exist in step 4c, are now located precisely by looking in a restricted region (as a consequence of the cup being physically positioned by keyed recess 70) and finding the centroid of the individual fiducial marks. This determines their exact locations within the camera field of view (i.e., 640×480).

4e(2) Based on the locations of the fiducial marks, the image is now rotated, translated, minified, and or magnified as necessary so that the resulting image has the fiducial marks 122 (and hence all other cap features) in "standard" positions which is hence presumed for all subsequent operations.

4e(3) Using a "map" of the features present on the cap top, each test is individually examined. Although the two test strips can in fact differ in the number of lines present and their specific locations, for the sake of simplicity, the operations on only one typical test strip will be described.

4e(4) Based on known default reference and drug line positions, non-overlapping rectangular regions 200 are "drawn" around each reference line 117R and drug line, e.g., 117D (FIG. 10B).

4e(5) For the region 200 which contains the reference line 117R, row sums are produced. The number of pixels summed for each row is the "width" of the test strip (e.g., 32 in FIG. 10C), the number of total row sums for each region is the "height" of the individual region (e.g., 48 in FIG. 10C). Each of these row sums produces a graph (FIG. 10D) whose X axis is related to the "height" of the region, and whose Y axis is related to the values of individual row sums. Let it be assumed that individual row sums will be smaller for darker horizontal rows and larger for lighter horizontal rows. The resulting graphs are then preferably normalized so that the Y axis values are between 0 and 100, and then subtracted from 100 so that the darkest row in a given region has the value 100 and the brightest row in a given region has the value 0. Bell shaped curves will result (presuming a drug or control line is present) as depicted in FIG. 10D.

4e(6) The reference line 117R must be located in order to proceed further and its exact position must be determined in order to locate the best estimated positions of the drug lines for further processing. The graph for the reference line is examined for a maximum value, which represents the reference line center position. After the center position is located, the regions drawn in substep 4e(4) above are redrawn to center the reference line and drug lines in their respective regions.

4e(7) For each drug region, row sums and the resulting graph are produced as described in substep 4e(5) above.

4e(8) Each drug region graph is divided into three equal parts, a left, center, and right part as represented in FIG. 10F. The drug line is presumed to occupy the center portion. However, its exact position and width can vary, and its brightness difference in relation to the neighboring area may be very subtle. Based on different wetting conditions, a dark condition in one region can in fact be lighter than a not-dark condition in another region. Hence, a relative mechanism is used to determine the presence or absence of a drug line.

4e(9) For each drug region graph, the total area under each of the three regions (left, center, right) is calculated. The left and right region areas are then numerically summed, and this resulting total area sum is multiplied by an experimentally determined "weighting value", thus producing a weighted sum. If the area of the center region is greater than this weighted sum, a decision is made that a line is present. If the area of the center region is less than or equal to the weighted sum, a decision is made that no line is present. By using urine samples with known drug concentrations, a weighting value of 0.75 has been found to produce very acceptable results. In order to conceptually understand what is going on, presume that the graph is perfectly symmetric and the drug line is centered in the graph, hence the graph will appear as a bell curve (FIG. 10F) (this is typical of the actual graphs produced) if a line is present, or at the other extreme, will appear as a flat line if no drug line is present. In the case of a flat line, then the summed areas of the left and right region will be exactly twice (2*X) the area of the center region (X). If the 2*X value is weighted by 0.75, the resulting area is now 1.5*X, which is greater than X. Hence no drug line is considered present. In fact, the weighting value would have to be less than 0.5 for a line to be considered present. As the center region grows in amplitude, its area reaches a point that it is now greater than the weighted sum of the left and right regions, and a line is considered present. Note that the presence or absence of a line is not determined by the exact position or shape of this curve, nor by the exact amplitudes of the dark and light components, which can vary widely based on various factors including the degree of wetting, the color of the urine, the particular lot of test strips, the time of exposure, extraneous material on the test strip, and shadows and/or reflections. All of these variations are compensated for in the relatively simple and concise mathematical procedure described which allows the presence or absence of drug lines to be repeatedly determined to a controllable, high degree of accuracy.

Once all adulteration test strips have been examined for color and all component test strips examined for visible lines, a final test result, for adulteration and identification of drug lines present and/or absent, is locally displayed and/or communicated to the host computer in accordance with aforementioned step 4f.

The foregoing describes applicants' preferred system for automatically testing fluid specimens to detect specific chemical components therein. The preferred system includes an assaying device comprised of a fluid collection cup and a cap carrying one or more test strips configured to produce visually discernable indications of the components of the specimen and/or specimen adulteration. The visual indications are read by an imager, e.g., digital camera, and interpreted by a processor which executes an analysis procedure to interpret the visual indications. The resulting test results are reported locally or via a communications network to a host computer. Thus, systems in accordance with the invention can quickly (e.g., in less than 15 minutes) and locally automatically test a fluid specimen to provide accurate qualitative test results. The system both assures the confidentiality of donor/specimen test results (by using machine readable, rather than human readable, markings) and a closely controlled chain of custody procedure.

Although a preferred embodiment has been described, it is understood that many modifications and variations will occur to those skilled in the art which fall within the intended scope of the invention as defined by the appended claims.

What is claimed is:

1. An apparatus for use with an assaying device presenting a lower periphery and including a test strip for providing a visual indication of at least one property of a fluid specimen, said apparatus comprising:

an apparatus housing including a base portion and a head portion,
said base portion having a keyed recess formed therein for receiving and holding the device in a fixed position relative to said head portion,
said keyed recess being complementary to the lower periphery of the assaying device to place the device in a specific orientation relative to said head portion;
a camera coupled to said head portion and operable to acquire an image of said test strip;
a processor operable to control said camera to periodically capture sequential images of said test strip, generate a digital representation of each captured image, and to process said digital representations to detect markings on said image indicative of each of said chemical components in said fluid specimen; and
output means for reporting the detection of said markings.

2. The apparatus of claim 1, further including a selectively actuated piston mounted in said head portion configured for contacting and engaging a portion of the device.

3. The apparatus of claim 1, further including:

a host computer;
a communication network; and wherein
said output means including a connectivity device for connecting to said host computer via said communication network.

4. The apparatus of claim 1, further including at least one light source for illuminating said test strip.

5. The apparatus of claim 1, further including a light shield movably mounted in said head portion for movement toward the assaying device to minimize stray light on said test strip.

6. The apparatus of claim 1, said base portion being fixed relative to said camera and configured to directly contact the device.

* * * * *